US010172762B1

(12) United States Patent
Branch et al.

(10) Patent No.: US 10,172,762 B1
(45) Date of Patent: Jan. 8, 2019

(54) V-BAND THERAPEUTIC WRAPPING SYSTEMS

(71) Applicants: Alan Branch, Paramus, NJ (US); Shirley T. Branch, Paramus, NJ (US)

(72) Inventors: Alan Branch, Paramus, NJ (US); Shirley T. Branch, Paramus, NJ (US)

( * ) Notice: Subject to any disclaimer, the term of this patent is extended or adjusted under 35 U.S.C. 154(b) by 445 days.

(21) Appl. No.: 14/852,746

(22) Filed: Sep. 14, 2015

Related U.S. Application Data

(63) Continuation-in-part of application No. 13/683,141, filed on Nov. 21, 2012, now abandoned.

(60) Provisional application No. 61/576,368, filed on Dec. 16, 2011.

(51) Int. Cl.
*A61H 23/00* (2006.01)
*A61H 23/02* (2006.01)
*A61F 7/03* (2006.01)
*A61F 7/02* (2006.01)

(52) U.S. Cl.
CPC ............ *A61H 23/02* (2013.01); *A61F 7/03* (2013.01); *A61F 2007/0219* (2013.01); *A61F 2007/0231* (2013.01)

(58) Field of Classification Search
CPC ...... A61F 7/02; A61F 7/007; A61F 2007/101; A61F 2007/0295; A61F 2007/0231; A61F 2007/0094; A61F 2007/0078; A61F 7/03; A61F 2007/0219; A61H 7/001; A61H 23/02; A61H 2201/0257; A61H 2201/0242; A61H 2201/0228; A61H 2201/0214; A61H 2201/0207; A61H 2201/10; A61H 2201/165; A61H 23/00; A61H 23/0218; A61H 23/0236; A61H 23/0245; A61H 23/0254; A61H 23/0263; A61N 2005/0659

See application file for complete search history.

(56) References Cited

U.S. PATENT DOCUMENTS

| 3,234,933 | A | * | 2/1966 | Martin | A61H 23/0263 601/41 |
| 4,979,502 | A | * | 12/1990 | Hunt | A61H 23/02 601/15 |
| 5,334,131 | A | * | 8/1994 | Omandam | A61H 23/0263 601/70 |
| 5,575,761 | A | * | 11/1996 | Hajianpour | A61H 23/0263 601/48 |
| 5,704,902 | A | * | 1/1998 | Vandenbelt | A61H 23/0263 601/46 |
| 2004/0260211 | A1 | * | 12/2004 | Maalouf | A61H 23/02 601/15 |
| 2005/0113724 | A1 | * | 5/2005 | Wriggle | A61H 23/02 601/46 |

(Continued)

*Primary Examiner* — Quang D Thanh
(74) *Attorney, Agent, or Firm* — Walter J. Tencza, Jr.

(57) ABSTRACT

A V-band therapeutic wrapping system including a V-wrap pad assembly with a V-wrap pad having; at least one vibrator-receiving-pocket or external Velcro attachment area with first color-coding; at least one endothermic/exothermic chemical reaction gel pack-pocket with a second color coding; a plurality of closers; at least one vibrator; at least one endothermic/exothermic chemical reaction gel pack; and at least one attaching strap. The V-wrap pad assembly is portable. The temperature and vibration treatment, as determined by a user-wearer, is provided by the V-band therapeutic wrapping system to target a core pain by enveloping selected the body surface when coupled to the user-wearer.

8 Claims, 13 Drawing Sheets

(56) References Cited

U.S. PATENT DOCUMENTS

| | | | |
|---|---|---|---|
| 2007/0090788 A1* | 4/2007 | Hansford | H01M 2/1055 320/107 |
| 2007/0149246 A1* | 6/2007 | Bodley | H04R 3/005 455/556.1 |
| 2007/0255187 A1* | 11/2007 | Branch | A61F 7/02 601/15 |
| 2009/0082705 A1* | 3/2009 | Asfora | A61H 19/00 601/46 |
| 2011/0071445 A1* | 3/2011 | Imboden | A61H 19/30 601/46 |
| 2012/0253236 A1* | 10/2012 | Snow | A61N 5/0618 601/2 |
| 2013/0204169 A1* | 8/2013 | Poepperling | A61H 9/0078 601/46 |
| 2015/0305974 A1* | 10/2015 | Ehrenreich | A61H 23/004 601/46 |
| 2017/0054120 A1* | 2/2017 | Templeman | H01M 2/1094 |

* cited by examiner

V-BAND THERAPEUTIC WRAPPING SYSTEMS

CROSS-REFERENCE TO RELATED APPLICATION

The present application is related to and claims priority from prior provisional application Ser. No. 61/576,368, filed Dec. 16, 2011; and parent application Ser. No. 13/683,141, filed on Nov. 21, 2012, which applications are incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

The following includes information that may be useful in understanding the present invention(s). It is not an admission that any of the information provided herein is prior art, or material, to the presently described or claimed inventions, or that any publication or document that is specifically or implicitly referenced is prior art.

1. Field of the Invention

The present invention relates generally to the field of wraps and braces in combination with endothermic/exothermic heat packs and vibration module, and more specifically relates to a V-band therapeutic wrapping system.

2. Description of the Related Art

Many individuals suffer from chronic pain, which is pain that lasts six months or longer. Encompassing a wide range of severity, chronic pain can be mild or agonizing, sporadic or incessant, simply inconvenient or completely crippling. According to the American Medical Association, the most common sources of pain stem from headaches, joint pain, pain from injury, and backaches. Additionally, various kinds of prevalent chronic pain include tendinitis, sinus pain, carpal tunnel syndrome, and pain affecting specific parts of the body, such as the shoulders, pelvis, knees, and neck. Pain of any sort is typically very undesirable, especially over a long duration.

Generalized muscle or nerve pain, experienced by people of all age groups, can also develop into a chronic condition. As the word "chronic" implies a seemingly endless cycle of recurring pain, it becomes necessary for individuals to seek ways to manage their pain, since complete eradication can be elusive. Having to fight through arthritic hands, knee flare-ups, and neck and shoulder pain in order to attend school, go to work, or to just take care of the demands of day-to-day life can be extremely challenging, since for the vast majority of individuals, life cannot come to a complete halt due to pain. This is particularly true for active persons, who experience pain on a regular basis. Whether a sports participant or exercise enthusiast, sore and strained muscles and joints are very common occurrences. Athletes and others suffering from such pain sometimes rely on analgesics and medications in the form of muscle relaxers or anti-inflammatory medication for light to moderate muscle pain and stiffness. A suitable alternative is needed.

Various attempts have been made to solve the above-mentioned problems such as those found in U.S. Pat. Pub. and U.S. Pat. Nos. 5,460,595; 6,866,644; 7,335,170; 6,554,787; 2007/0197941; and U.S. Pat. No. 4,979,502. This prior art is representative of therapeutic wraps and braces. None of the above inventions and patents, taken either singly or in combination, is seen to describe the invention as claimed.

Ideally, a V-band therapeutic wrapping system should be user-friendly and, yet would operate reliably and be manufactured at a modest expense. Thus, a need exists for a reliable V-band therapeutic wrapping system to provide comfort and to avoid the above-mentioned problems.

BRIEF SUMMARY OF THE INVENTION

In view of the foregoing disadvantages inherent in the known wrapping and therapeutic device art, the present invention provides a novel V-band therapeutic wrapping system. The general purpose of the present invention, which will be described subsequently in greater detail, is to provide effective therapeutic relief.

A V-band therapeutic wrapping system is disclosed herein, in a preferred embodiment, comprising: a V-wrap pad assembly including a V-wrap pad or V-wrap strap having at least one vibrator-receiving-pocket comprising at least one first color-coding; at least one endothermic/exothermic chemical reaction (or) gel pack-pocket which preferably comprises a second color coding; a plurality of closers; at least one vibrator; at least one endothermic/exothermic chemical reaction gel pack; and at least one attaching strap. The V-wrap pad assembly is portable. The temperature and vibration treatment, as determined by a user-wearer, is provided by the V-band therapeutic wrapping system to target a core pain by enveloping selected the body surface when the device is coupled to the user-wearer. The V-wrap pad assembly comprises an adjustable support-brace during an in-use condition. The V-wrap pad is flexible and conformable to the body surface and comprises breathable fabric and may be formed of an elastic material.

The vibrator(s) preferably comprise wave, pulse and steady settings, the vibrator(s) independently powered via at least one D/C power battery. Further, the vibrator(s) comprise off, low, medium and high frequency-settings. The vibrator(s) are able to be inserted and (temporarily) enclosed in at least one of the vibrator-receiving-pocket(s) or attached externally via Velcro. The vibrator(s) are reconfigurable at the discretion of the user-wearer and use of the endothermic/exothermic chemical reaction gel packs are part of a selectable configuration about a desired body surface. The vibrator(s) are able to be used to facilitate blood flow and healing.

The endothermic/exothermic chemical reaction gel pack(s) are able to be inserted in at least one of the endothermic/exothermic chemical reaction (or) gel pack-pocket(s). It should be noted that other chemical reaction devices and means may be used other than gel-versions to add/remove heat for treatment. The V-wrap pad assembly also preferably comprises color coded placement areas to indicate where a majority of the user-wearer(s) find maximum relief for placement of the vibrator(s) using the first color-coding and the endothermic/exothermic chemical reaction gel packs using the second color-coding. The endothermic/exothermic chemical reaction gel pack when comprising a heating pack is useable to increase a temperature of the V-wrap pad to provide at least one heating therapeutic effect. The endothermic/exothermic chemical reaction gel pack when comprising a cooling pack is useable to decrease a temperature of the V-wrap pad to provide at least one cooling therapeutic effect. Heating and cooling may be used separately, together or in combination to create the desired effect. The V-wrap pad is able to be used to reduce inflammation and/or provide a warming effect to reduce pain.

The plurality of closers preferably comprise fasteners which are useable to repeatedly close and open the vibrator-receiving-pocket(s) and the endothermic/exothermic chemical reaction gel pack-pocket(s). The fasteners of the plurality of closers may comprise hook and loop fasteners. The attaching strap(s) are able to removably attach the V-wrap pad adjacent a body surface.

A kit for the V-band therapeutic wrapping system is also disclosed herein preferably including: a V-wrap pad assembly with a V-wrap pad with vibrator-receiving-pockets and endothermic/exothermic chemical reaction gel pack-pockets (both color-coded); vibrators (vibrating devices); endothermic/exothermic chemical reaction gel pack s (heat packs and/or cold packs); and a user instruction manual. Many V-wrap pad assemblies may be included for different portions (parts) of the body.

A method of using a V-band therapeutic wrapping system is also disclosed herein preferably comprising the steps of: wrapping a V-wrap pad assembly about a body surface; strapping the V-wrap pad assembly adjacent the body surface to therapeutically-treat a partially enveloped body region; inserting vibrators and endothermic/exothermic chemical reaction, or gel packs into color-coded vibrator-receiving-pockets and endothermic/exothermic chemical reaction gel pack-pockets respectively; and activating the vibrators and the endothermic/exothermic chemical reaction gel pack s selectively to provide relief to the body region (or part). The method may be used on different regions of the body.

An alternate embodiment of the "vibrator(s)" is formed as a vibration module called a "VPOD" or a "V-Pod". As such the V-Pod has a curved profile (including concave and convex surfaces) that allow it to conform to the curvature of a person's body. Further the curved profile allows the user to apply a plurality of V-Pods to one body area to "surround" a chosen body part and form a "Sphere of Vibrations" around it for maximum effect and benefits. The V-Pod incorporates a rotary vibration motor or the like; rechargeable batteries or the like; a firmware board or the like controlling vibration velocity, intensity, and speeds; and a remote control mechanism. The V-Pods can be controlled remotely individually or in unison using a number of known methods, arrangements, and mechanisms, including computer applications software on a remote control unit or smart phone. The V-Pod is charged using an associated charging base or the like that can be plugged into a wall outlet or any other source that provides appropriate electric power.

A "Sphere of Vibration" is a concept that we discovered during 20-years of testing. Placing a single point of contact for vibration on a joint may provide some relief, but in many cases it is insufficient. By placing points of vibration and thermos therapy in 3 or more strategic places particularly around joints, it give the feeling of encasing the affected area in a "Sphere of Vibration" and provides advanced relief.

The present invention holds significant improvements and serves as a V-band therapeutic wrapping system. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, V-band therapeutic wrapping system, constructed and operative according to the teachings of the present invention.

The various embodiments of the present invention will hereinafter be described in conjunction with the appended drawings, wherein like designations denote like elements.

DETAILED DESCRIPTION

Figure 1:
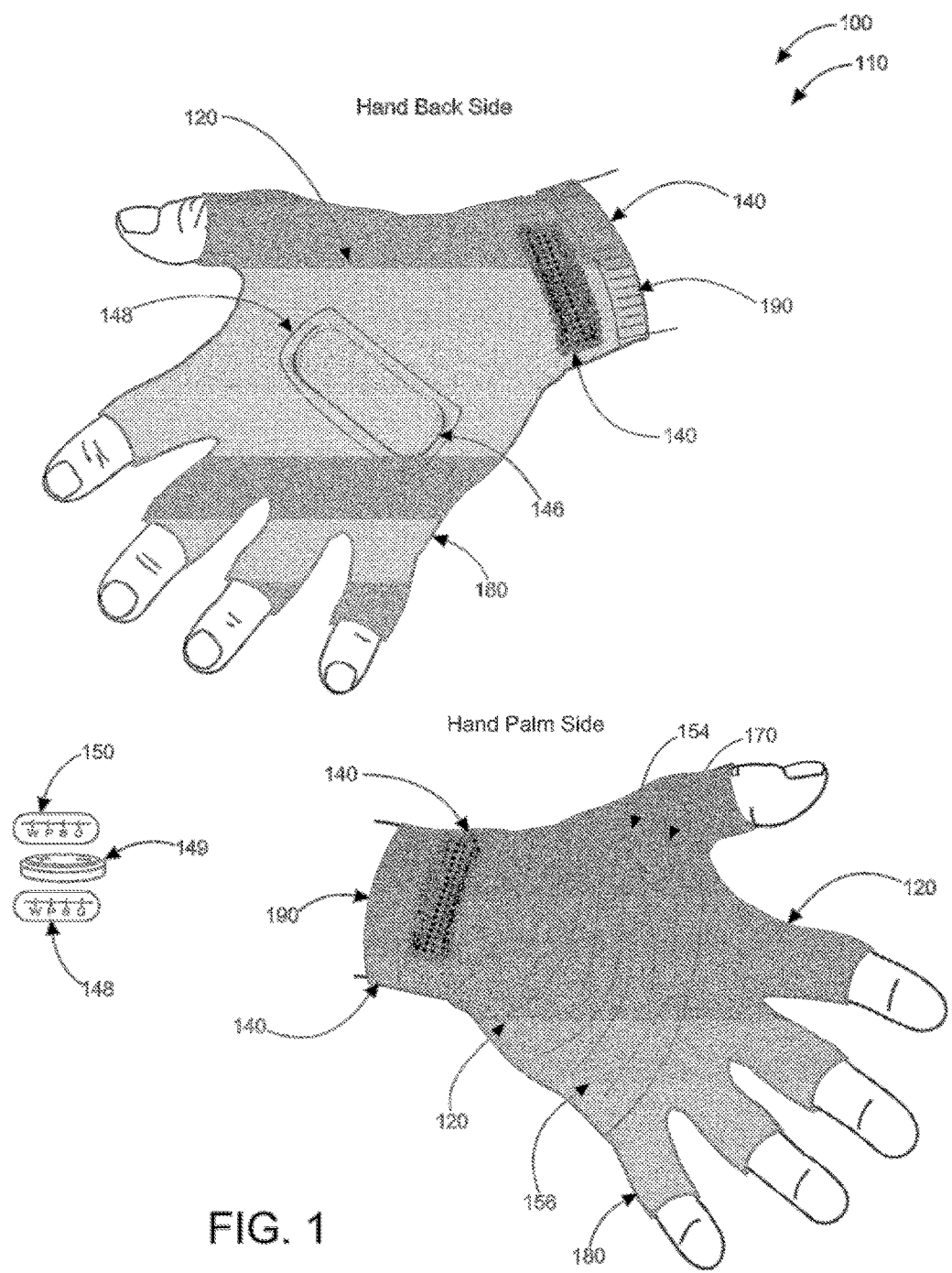
FIG. 1 shows a perspective view illustrating a V-wrap pad assembly of the V-band therapeutic wrapping system for use on a hand and wrist region in an in-use condition according to an embodiment of the present invention.

As discussed above, embodiments of the present invention relate to a therapeutic device and more particularly to a V-band therapeutic wrapping system, a line of wraps specially designed for areas of the body that experience muscle and joint pain that combines vibration along with heat/cold therapy for pain relief. Design intent is to provide a therapeutic device that can be worn on the person and be effectively used while 'on the go'.

Generally speaking, the present invention comprises a line of wraps or straps, specially designed for areas of the body that experience muscle and joint pain, that combines vibration along with heat/cold therapy for pain relief that can be worn on the person. The device is portable for ease of use, transport and storage.

The present invention provides a convenient solution to challenges that can be encountered with pain management. The V-band therapeutic wrapping system (VBand) comprises a line of specially designed, wrap-around apparatuses configured with multiple vibrating capabilities as well as hot and cold therapy. As such, the line offers a multifaceted pain management tool that provides mobile topical treatment, even while on the go. The braces that comprise the VBand line are targeted to specific areas of the body, or the areas that most commonly experience muscle, joint, and nerve pain. Sized appropriately for the afflicted areas, these braces may include wraps for the ankle/foot, elbow, shoulder, neck (not shown in drawings), full back, lower back, hip, knee, wrist, hand and fingers. The V-band wraps will preferably come in at least 6 different sizes for different sized people. The sizes preferably include but are not limited to: XS, S, M, L, XL, and XXL. The difference in the sizes will be found in between the adjustable straps and expandable, breathable fabric.

Other body portions may apply. Fashioned of a durable fabric material, each VBand wrap is preferably equipped with strips of the hook and loop system commonly known as Velcro® to facilitate security adjacent to the body or around the body part. For optimal comfort, the units also preferably feature breathable, stretchable elastic that allow for easy adjustability.

The VBand system of braces is further therapeutic because of its vibrating and hot/cold capabilities. Each wrap may be packaged with two or three (2 or 3) battery-operated vibration modules, or compact, rectangular, or other shaped units with an internal vibrating element(s). These components may be accompanied by detailed instructions for placement in order to achieve optimal benefits. It should be noted that the multiple modules create a sphere of vibration therapy, thoroughly encasing the affected area. The device(s) may be powered by small, industry standard, long-lasting batteries such as pancake batteries (or the like) which weigh less and are more streamlined (than AA or AAA versions) and thus decrease the overall size of the individual vibration units. It should be noted that the final decision on the battery type will be up to the manufacturer, but preference is a pancake battery due to size and weight. The batteries may also comprise rechargeable versions.

The vibrators also comprise a small footprint; use of commercial vibrators is preferred. It is possible to use the vibration units independently of the wraps on regular clothing or other type braces, although for best results it isn't recommended. Two (2) slide-operated switches for vibration frequency may also be used. The module may be backed with Velcro®. The vibration packs can also be inserted into the exterior or interior heat/cold packet, pockets as well. They can even be piggy backed with the hot/cold packs.

It should be noted that the Vibration module is meant to utilized in two versions. In the first version, the Vibration module is attached externally by Velcro to the exterior color designated or looped areas of wrap. In the second version, the vibration modules are inserted into interior pockets along with the hot/cold packs. Further modifications of this can be suggested by the licensing manufacturer. The Vibration modules have the hook portion of the hook and loop fastener (Velcro®) and may be removably-attached to other OTC wraps or outer clothing, but it is not recommended.

This piece of material/module may be secured directly onto the brace, at indicated points or at the points where the pain is most acute. As such, the vibration therapy can be easily relocated as needed, whether on top of the foot or above the ankle, underneath the wrist or on top of the hand, on the left side or the right side of the back, and so on. Providing "on demand" treatment, the vibration preferably works to interfere with an afflicted nerve's ability to transmit pain. Additionally, the vibration facilitates blood flow and healing. The VBand's second component of therapy, the use of heat and cold to reduce inflammation, is achieved via a series of pouches (pockets) strategically placed along the braces. These pouches removably house cold/heat packs, which may be gel-packed units that are kept in a freezer or warmed in a microwave or snap-activated heat/cold packs to provide the temperature desired. An individual may put the vibration device into these pockets/pouches as well if they like. Since there are several pouches for each VBand brace, the packs could be inserted at the points where therapy is needed most, in the same manner as the adjustable vibration module.

The VBand system provides consumers an all-encompassing tool for chronic, sports-induced, exertion-induced, and minor pain management. An inventory of specially designed wraps or straps configured for several areas of the body, this novel system allows sufferers of a variety of ailments to easily and expediently apply topical therapy. Offering a two pronged approach to pain management, the VBand's dynamic duo of vibration and heat/cold substantially ensure that throbbing pain, searing inflammation, and uncomfortable swelling are swiftly alleviated. Eliminating the need to be tied to stationary forms of pain therapy, these wearable wraps allow consumers to attend to their maladies wherever they may be, whether driving in a car, walking through a mall, sitting at a desk in their office, or simply reclining in front of the television. In this manner, the VBand returns chronic pain sufferers to their lives, allowing them to go about virtually any desired activity as they wish. Fabricated of durable, high quality materials and components, this system will withstand years of continual use. It should be noted that the present invention is an over-the-counter (OTC) therapeutic device and when an individual component of the V band system needs to be replaced, that one component can be replaced individually without replacing the entire VBand unit. Replacements may be available online for convenience.

The VBand line may be expanded to include a "medical durable" version intended for use by sports teams at physical therapy offices, doctor's offices, hospitals, and other recovery facilities. In brief, this version may be larger, and may be operated via electrical power or portable rechargeable external battery packs. Battery packs may be attached to hospital beds for post surgical applications for example a few days after joint/hip surgery, or on sports fields where no immediate power is available. These units may also have a/c plug in adapters for when power is available. It should be noted that the medical durable version will not be made of the same material as the OTC version. This unit will be made to medical standard of easily cleanable materials that can be "sterilized" with hospital standard disinfectant liquids. Further, these units will be heavier and made to be used while the patient is under at least partial supervision.

The "medical durable" version may prove ideal for patients who may be bedridden or at medical facilities. The VBand provides much needed therapy to a wide array of joint and muscle ailments. Wearable and portable, this practical system allows for easy manipulation of therapeutic application, regardless of the location of the pain.

The medical durable version's mobility problem is resolved in this manner. Each independent unit is a completely autonomous vibration/heating unit attached to the master control unit by a pair of light weight double wire sets ending in multi-function plugs that plug easily into the controller (only in the medical durable version). Each pain relief unit will draw its power through the master control unit via one of the double wire sets.

The master control is be able to accommodate 4 or more independent body mobile pain relief units; ie: 2-knee & 2-elbow or 1-knee, 1-elbow, 1-shoulder, 1-lower back. The master control unit preferably obtains power from either of two sources: Standard A/C plugs with A/C-D/C transformer for when the user is stationary either in bed or seated; or via a battery belt utilizing the latest in flat, notebook or video camera battery technology. The batteries may be slid into special conductor receiver sleeves along the belt which fastens with Velcro® (hook and loop) around the waist of the wearer. This is an option available, not common to all medical durable units. This would be good for surgical recovery centers. For example: knee or hip replacement centers. This would aid during physical therapy sessions where the patients have high levels of pain. It would aid them while minimally restricting their physical therapy exercises. The vibration units on these particular versions may be more powerful in these units because the pain would be more intense and the batteries are larger and able to provide more power for dealing with greater pain.

It should also be mentioned that the vibration units would be more powerful in these units because the pain would be more intense and the batteries are larger and able to provide more power. Size isn't so much a consideration in these units because they are meant to be used in medical facilities under partial supervision.

A heavier double wire set attaches the power source of the belt to the master control unit which will also be fitted with hook and loop to attach to the belt or slip in a special pocket.

The master controller makes use of soft key or membrane technology along with standard adjustment bar slide technology. The controller can have 4 double receptors, one for each of the at least 4 independent pain relief units.

Associated with each dedicated port set is preferably an independent control set including a slider or buttons or membrane control for vibration intensity, 4 heat settings (off, low, medium, hot) and 4 vibration type selection buttons, (off, pulse, wave, steady). It has been determined that not only do specific vibratory wave lengths cause differences in relief of pain, but different types of vibration also have an effect on different pains. For example, more intense pain can sometimes be alleviated better by wave vibrations instead of pulse or steady vibration. In the present invention the user may choose which mode best suits his/her purpose for pain relief.

For mobile mode, the sliders will not change the settings until an "unlock" button is depressed to prevent the accidental changing of vibration during arm swinging or slipping of unit into its belt pouch. To prevent accidental heat control change, each soft heat button must be held for a minimum of 2-seconds to cause a setting change. To prevent injury due to the over application of heat, a sensor in each unit will automatically shutdown the heating units when they reach a certain pre-specified temperature to be determined by a qualified M.D. Current PC heat sensor technology can be utilized for this at minimal cost.

The main purpose of the V-Band system is to afford mobile pain relief through vibration stimulus of the affected area's nerve endings. By using different vibration wave length and vibration motifs this unit confuses the nerve endings into transmitting the signal of vibration instead of pain. It is a simple, un-intrusive, effective method for pain relief. Since it utilizes off-the-shelf materials in its design it is easy to build and replace individual parts.

This system is designed for each body area and it's removable, replaceable and adjustable vibration units can be directly around the affected areas. Due to its design, it is not tied to an A/C outlet and is fully mobile so it can be used at home, in the office, driving or even walking in public.

The V-band therapeutic wrapping system may be used on a wide array of body surfaces, as previously mentioned. When the V-band therapeutic wrapping system is to be used on a hand and wrist region (as shown in FIG. 1) hook and loop (Velcro®) closures affix around the wrist and hand with the area around the hand itself comprising elastic material that permits the affixing of Velcro® (hook and loop) fasteners to it. The entire area round the hand itself up to and including the knuckles and bottom half of the thumb are covered with hook and loop attachable fabric to enable the attachment of hook and loop attachable vibration modules. The flap that includes the secondary finger ice/heat packs are attachable via hook and loop strip to the ½ glove. The flip over flap will come with a separate set of pockets and can even come with specially designed ice/heat gel packs that can fit into it. The primary reason for the cover over the loop section of the Velcro is to keep it from getting full of clothing lint, etc. This option may be eliminated if needed during the manufacturing process. This applies to all the V-Band wraps.

The interior of V-band therapeutic wrapping system when used on the hand and wrist region includes an extended soft fabric, hook and loop sectioned pocket designed for hold heat/cold packs. Further, preferably there are hook and loop squares strategically placed throughout the pocket to separate the pockets into smaller areas to either accommodate smaller ice/heat packs or keep larger ones from slipping around the joint. The cold/heat packs can be designed to fit the entire pocket. When using the standard hot/cold packs, hook and loop closers are strategically placed throughout this pocket area to permit the heat/cold packs to be moved anywhere around the shoulder that the person needs relief. It also will enable the wearer to use any OTC ice/heat pack available.

The brace as shown in FIGS. 1-6 also preferably comprises color-coded placement areas to indicate where most people find the most relief for placement of hot and cold packs (as a guideline for use), keeping in mind that by creating a sphere or encompassing of the joint in vibration will provide the effect desired which is to alleviate pain through nerve conduction of vibration with the associated heat or cold. In this way the present invention is made more user-friendly and effective in-use.

When a smaller version of the standard hot/cold packs are used, they provide more targeted relief. If smaller hot/cold packs are used, they may not fit into the supplied pockets. The customized smaller version of the standard hot/cold packs slips over the fingers and addresses knuckle and lower finger issues or the hot/cold packs may slip over the hand & thumb and addresses thumb arthritis issues.

For powering V-band therapeutic wrapping system when used on the hand and wrist region 2 Pancake batteries may be used for example (other powering means may also be used). A smaller single Pancake, remember slimness of the vibration unit is very import and battery unit can be made available as well. If the Vibration Modules that come with the hand unit are not strong enough for the individual, the user may purchase more or stronger modules and attach them just as easily.

Each of the vibration modules (as shown in embodiments of FIGS. 1-6) preferably include two adjusters on it, one for motif (Wave, Pulse, or Steady) vibration and one for Frequency, (off, low, medium, or high). Further, each of the vibration modules can be set individually by the user for best results. If one of the vibration modules wears out, it can be easily replaced since they are not fixed to the holders in the present design. These vibration modules are connected to the brace by hook and loop tabs attached to the actual module or inserted into removable/attachable pockets affixed by hook & Loop Velcro or stationary pockets.

It should be understood that the heat/cold packs used in FIGS. 1-6 as subsequently described can be supplied by manufacturer to the sizes required for the different size pockets or other third party packs can also be inserted including the squeeze or snap activated chemical heat/cold packs.

Figure 2:
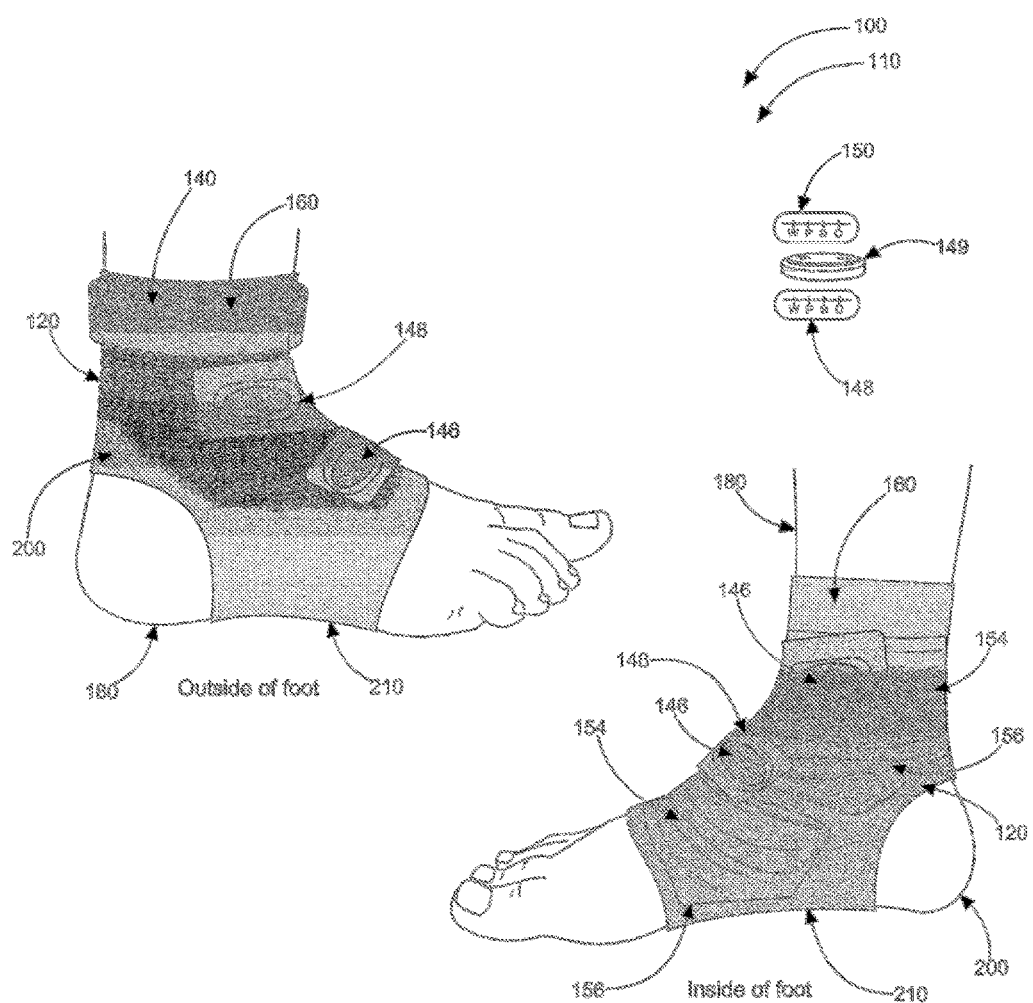
FIG. 2 shows a perspective view illustrating a V-wrap pad assembly of the V-band therapeutic wrapping system for use on a foot and ankle region in an in-use condition according to an embodiment of the present invention.

When the V-band therapeutic wrapping system is to be used on a foot and ankle portion (as shown in FIG. 2). The foot and ankle brace may be a slip-over elastic support ankle brace or a closable hook & anchor Velcro support wrap or both versions. It is up to the manufacturer that licenses the patent. Note that each brace will come in several sizes to accommodate differently sized people and enables the attachment of a plurality of hook and loop attachable vibration modules.

The interior of V-band therapeutic wrapping system when used on the ankle and foot region preferably includes an interior, against the skin, soft cloth pocket designed to hold heat/cold packs. There are hook and loop (Velcro®) squares strategically placed throughout the pocket to separate it into smaller areas to either accommodate smaller ice/heat packs or keep larger ones from slipping around the joint and to allow placement to the wearers desire. Velcro® closers are strategically placed throughout this pocket area to permit the heat/cold packs to be moved anywhere around the foot and ankle portion that the person needs/desires relief. For powering V-band therapeutic wrapping system when used on the foot and ankle region 2 pancake batteries may be used. However, for all of the standard sized areas like knees, ankles, elbows, hands and feet; pancake or larger batteries may be used (the final decision is up to manufacturer's discretion) due to slimness and weight playing key factors in mobility and comfort for use everywhere due to size of vibration units.

Figure 3:
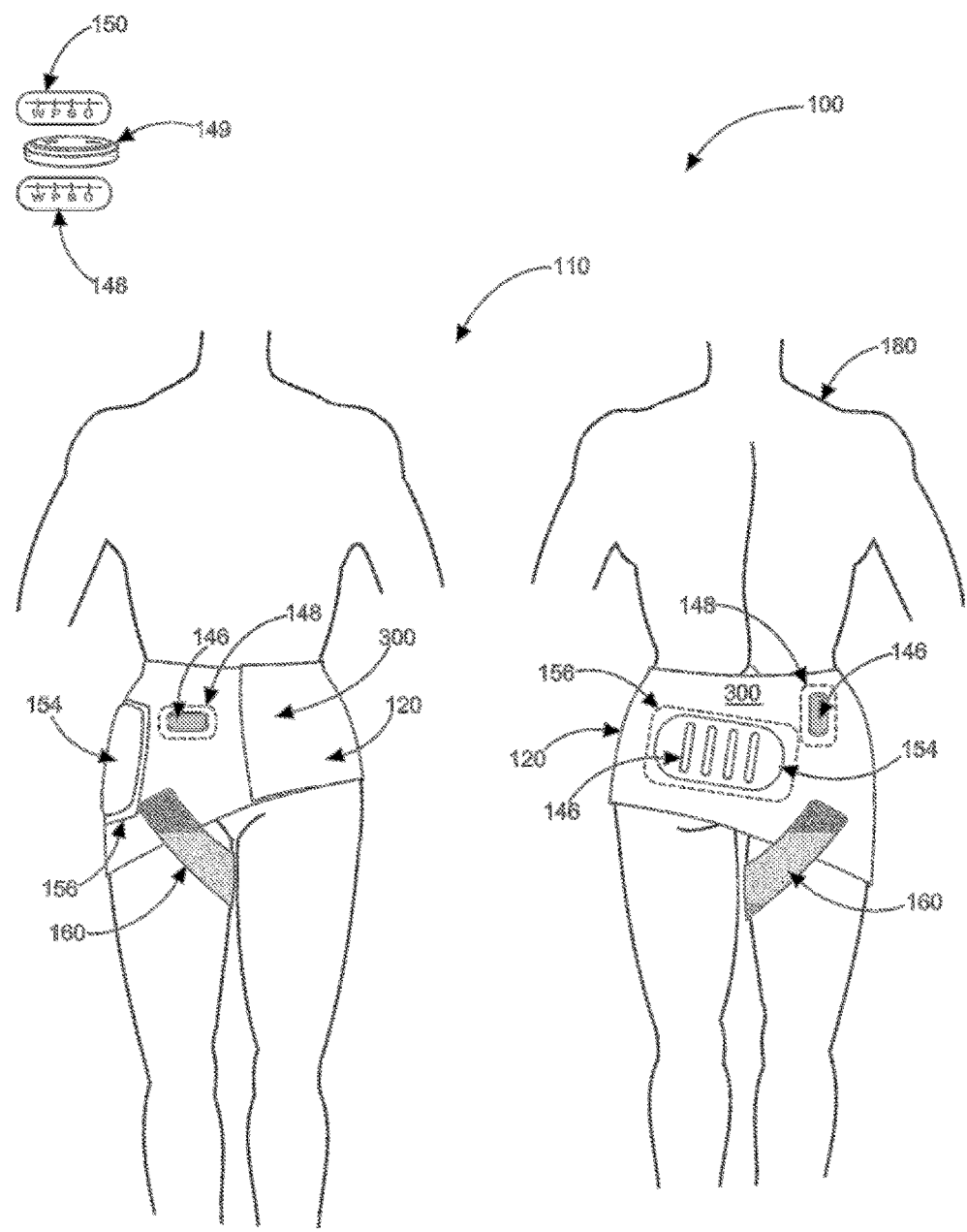
FIG. 3 shows a perspective view illustrating a V-wrap pad assembly of the V-band therapeutic wrapping system for use on a lower back and hip region in an in-use condition according to an embodiment of the present invention.

When the V-band therapeutic wrapping system is to be used on a lower back and hip region (as shown in FIG. 3), hook and loop material is adjustable around a waist and a lower/mid abdomen expandable fabric sheath/brace and covers almost the entire area around the lower back and hip joint to enable the attachment of Velcro® attachable vibration modules. The interior of V-band therapeutic wrapping system when used on the lower back and hip region includes an extended soft fabric, Velcro® sectioned pocket designed to hold heat/cold packs.

Since these pockets are designed to permit the placement of ice/heat packs anywhere, hook and loop closers are strategically placed throughout. These closers permit the wearer to adapt the pocket to any size ice/heat pack in virtually any location, front, back or side where the person needs relief. For powering the V-band therapeutic wrapping system for use on the lower back and hip region, the present invention is powered by 4 AA batteries in a longer and slightly larger module embodiment. If this is not sufficient for the individual larger vibration modules that use up to 8 AA batteries may be available. Once again, the final battery choice is up to the manufacturer. The key in deciding which battery to use as stated above is finding a balance between power of vibration, length of battery life, weight and size of vibration units for comfort of wearer.

Figure 4:
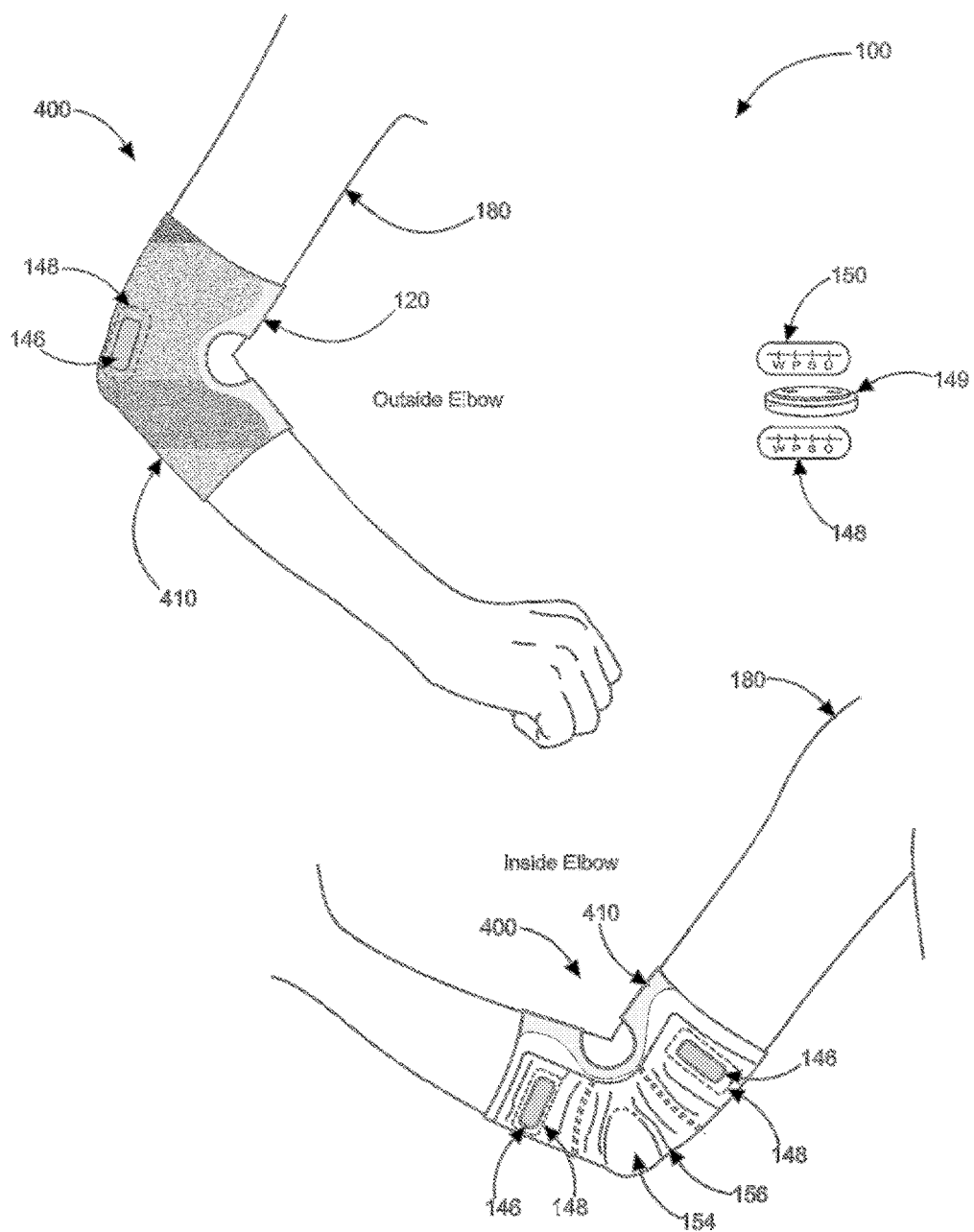
FIG. 4 shows a perspective view illustrating a V-wrap pad assembly of the V-band therapeutic wrapping system for use on an elbow region in an in-use condition according to an embodiment of the present invention.

When the V-band therapeutic wrapping system is to be used on an elbow portion (as shown in FIG. 4) hook and loop portion is adjustable over the elbow expandable fabric sheath/brace or the brace may be a slip-over elastic support elbow brace and enables the attachment of hook and loop attachable vibration modules. The interior of V-band therapeutic wrapping system when used on the elbow region includes an interior, against the skin, soft cloth pocket designed to hold heat/cold packs. There are hook and loop squares strategically placed throughout the pocket to separate it into smaller areas to either accommodate smaller ice/heat packs or keep larger ones from slipping around the joint and to allow placement to the wearers desire.

Special cold/heat packs can be designed to fit into the V-band therapeutic wrapping system for an elbow portion to cover the entire joint by filling the entire pocket. The V-band therapeutic wrapping system for an elbow portion is also deigned to accept any OTC (over-the-counter) ice/heat pack already on the market. Hook and loop closers are strategically place throughout this pocket area to permit the heat/cold packs to be moved anywhere around the elbow portion that the person needs relief. For powering V-band therapeutic wrapping system when used on the elbow region pancake or larger batteries may be used at the discretion of the manufacturer.

Figure 5:
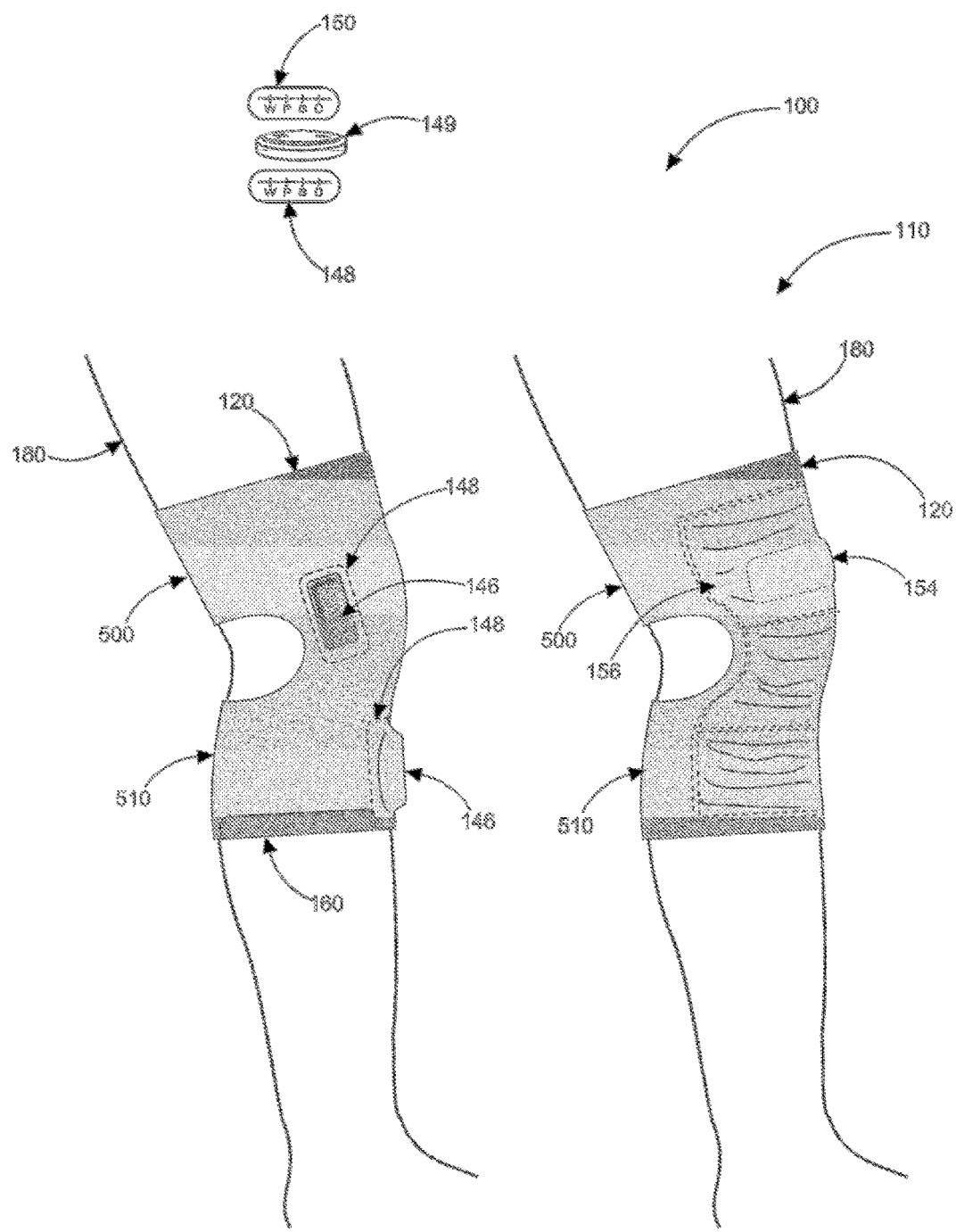
FIG. 5 shows a perspective view illustrating a V-wrap pad assembly of the V-band therapeutic wrapping system for use on a knee joint region in an in-use condition according to an embodiment of the present invention.

When the V-band therapeutic wrapping system is to be used on a knee portion (as shown in FIG. 5). Velcro is adjustable over the knee expandable fabric sheath/brace or the brace may be a slip-over elastic support or Velcro adjustable knee brace and enables the attachment of a plurality of Velcro® (hook and loop) attachable vibration modules. If the vibration modules that come with the knee unit are not big or strong enough for the person they can purchase more or larger more powerful V-band vibration modules and attach them just as easily.

The interior of V-band therapeutic wrapping system when used on the knee region includes an interior, against the skin, soft cloth pocket designed to hold heat/cold packs. There are hook and loop squares strategically placed throughout the pocket to separate it into smaller areas to either accommodate smaller ice/heat packs or keep larger ones from slipping around the joint and to allow strategic placement according to the wearer's desire. Velcro® closers are strategically place throughout this pocket area to permit the heat/cold packs to be moved anywhere around the knee portion that the person needs relief. For powering V-band therapeutic wrapping system when used on the knee region 2 pancake or larger (rechargeable or non-rechargeable) may be used. As previously noted, pancake or larger batteries may be used (the final decision is up to manufacturer's discretion) due to slimness and weight playing key factors in mobility and comfort for use everywhere due to size of vibration units.

Figure 6:
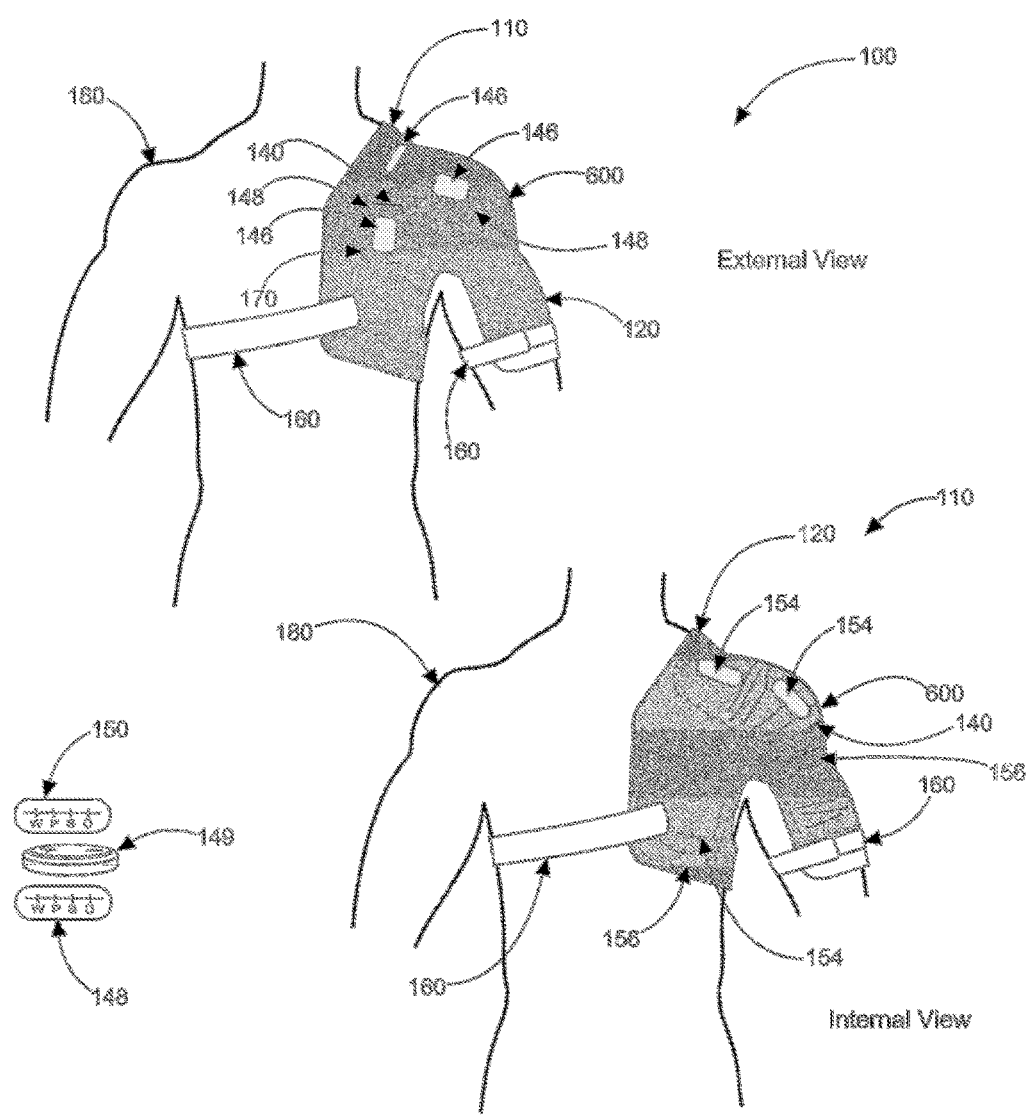
FIG. 6 shows a perspective view illustrating a V-wrap pad assembly of the V-band therapeutic wrapping system for use on a shoulder joint region in an in-use condition according to an embodiment of the present invention.

When the V-band therapeutic wrapping system is to be used on a shoulder region (as shown in FIG. 6) Velcro® is adjustable over the shoulder fabric sheath/cover and covers almost the entire area around the shoulder joint to enable the attachment of Velcro® attachable vibration modules. The interior of V-band therapeutic wrapping system when used on the shoulder region preferably includes an extended soft fabric, Velcro® sectioned pocket designed to hold heat/cold packs. Velcro® closers are strategically place throughout this pocket area to permit the heat/cold packs to be moved anywhere around the shoulder that the person needs relief. It also will enable the wearer to use virtually any OTC ice/heat pack available. For powering V-band therapeutic wrapping system when used on the shoulder region 2 AA batteries or 4 AA battery units, in a longer or slightly wider module may be used. If this is not sufficient for the person larger vibration modules powered by up to 8 AA, batteries may be available. As previously noted, pancake or larger batteries may be used (the final decision is up to manufacturer's discretion) due to slimness and weight playing key factors in mobility and comfort for use everywhere due to size of vibration units.

In addition to the OTC version listed above there is a Medical Durable version (embodiment) that is intended for use in doctor's offices, PT offices, recovery centers or hospitals. In this rendition the units comprise the capability to be plugged into power sources or use larger battery sources that are intended for longer uses. Hospital versions may have attachment hooks so the rechargeable battery packs can be hung from patient beds etc. The battery pack strap-on belt mentioned earlier may also be used. The units may be made of durable, cleanable hospital grade materials that can be sterilized with medical cleaning solutions to promote the health of users. Medical Durable versions may comprise various add-on features and do not need to be as portable as OTC versions. As a result they may comprise heavier materials, larger batteries, more support and the like for longer and more vigorous treatments to be applied.

To direct the vibration to the part of the body where it is required, there has to be specific molds designed to be applied to that area. These individual molds would be fastened with Velcro® (hook and loop) and the non-heat or vibration areas are preferably constructed of light-weight elastic material that breathes with the vibration units inserted in specific areas within the mold. Other models would be made of thicker terry clothe type material also fastened with Velcro®.

To direct heat or cold to the needed areas, the delivery system cannot be flat and overtly thick as most pads today. It cannot be chemically induced heat or cold because these packets never achieve substantial enough heat or cold to have the desired effect on arthritis or chronic pain. Again, molding to specific body areas is required. Instead of large bulky single flat units, multiple interconnected small padletts are to be utilized. These padletts working in unison generate a field of warmth that penetrates even through clothing. To concentrate the effect there needs to be special molds not only for each specific body area, but in multiple sizes to accommodate the variance in human anatomy. In this way the present invention increases its relative effectiveness.

Referring now to the drawings more specifically by numerals of reference there is shown in FIGS. 1-6, perspective views illustrating V-wrap pad assembly 110 for use on various joints and appendages on the body of the V-band therapeutic wrapping system 100 in in-use conditions according to embodiments of the present invention.

V-band therapeutic wrapping system 100 preferably comprises: V-wrap pad assembly 110 including V-wrap pad 120 having at least one vibrator-receiving-pocket 148; at least one endothermic/exothermic chemical reaction gel pack-pocket 156; a plurality of closers 140; at least one vibrator 146; at least one endothermic/exothermic chemical reaction gel pack 154; and at least one attaching strap 160. V-wrap pad assembly 110 is preferably portable. V-wrap pad assembly 110 may be worn over or under clothing of user-wearer 180. Further, V-wrap pad assembly 110 is completely mobile in preferred embodiments and can be worn and used virtually anywhere, including while driving without restrictions. V-wrap pad assembly 110 may also be worn and used while in motion and not confine user-wearer 180 to be restricted to a chair, bed or within a certain vicinity to a power source. Pockets may be larger or smaller than shown in the drawings; further there may be less or more of the pockets than shown.

Attaching strap(s) 160 are able to removably attach to V-wrap pad 120 adjacent a body surface. Body surface may include but is not limited to hand and wrist region 190 as illustrated in FIG. 1; foot and ankle region 200 as illustrated in FIG. 2; lower back and hip region 300 as illustrated in FIG. 3; elbow region 400 as illustrated in FIG. 4; knee joint region 500 as illustrated in FIG. 5; and shoulder joint region 600 as illustrated in FIG. 6.

V-wrap pad 120 is flexible and conformable to the body surface. The temperature and vibration treatment as determined by user-wearer 180 is provided by V-band therapeutic wrapping system 100 to target a core pain by enveloping the body surface when coupled to user-wearer 180 as illustrated in FIGS. 1-6. V-wrap pad assembly 110 may also comprise an adjustable support-brace including foot and ankle support brace 210 as shown in FIG. 2, elbow support brace 410 as shown in FIG. 4; and knee support brace 510 as shown in FIG. 5 during an in-use condition.

V-wrap pad 120 preferably comprises breathable fabric (light-weight elastic material). Upon reading this specification, it should be appreciated that, under appropriate circumstances, considering such issues as user preferences, design preference, structural requirements, marketing preferences, cost, available materials, technological advances, etc., other materials such as, for example, thicker terry-cloth type, or other suitable fabrics, etc., may be sufficient.

V-wrap pad assembly 110 preferably comprises color coded placement areas 170 to indicate where a majority of user-wearer(s) 180 find maximum relief for placement of vibrator(s) 146 and endothermic/exothermic chemical reaction gel pack s 154, an extremely useful and novel feature. Further, vibrator(s) 146 are able to be used to facilitate blood flow and healing, making it multi-functional. V-wrap pad 120 is preferably able to be used to reduce inflammation via nerve conduction of vibration (via vibrator(s) 146) with the associated heat or cold from endothermic/exothermic chemical reaction or gel packs 154.

Endothermic/exothermic chemical reaction gel pack (s) 154 are preferably able to be inserted in at least one of endothermic/exothermic chemical reaction or gel pack-pocket(s) 156. Other 3$^{rd}$ party endothermic/exothermic chemical reaction gel pack (s) 154 can also be inserted including the squeeze or snap activated chemical heat/cold packs. Endothermic/exothermic chemical reaction gel pack 154 is preferably used to increase relative temperature of V-wrap pad 120 to provide at least one heating therapeutic effect. Endothermic/exothermic chemical reaction gel pack 154 is preferably also used to decrease relative temperature of V-wrap pad 120 to provide at least one cooling therapeutic effect. Combinations heating/cooling effects may be employed as needed.

Vibrator(s) 146 are able to be inserted and enclosed in at least one of vibrator-receiving-pocket(s) 148 as selected by user-wearer 180. Vibrator(s) 146 are reconfigurable at a discretion of user-wearer 180 and use of endothermic/exothermic chemical reaction gel pack (s) 154 are part of a selectable configuration about a desired body surface. Vibrator 146 preferably comprises two adjuster settings, first adjuster setting 148 and second adjuster setting 150. First adjuster setting 148 is for motif with vibrator(s) 146 comprising wave, pulse and steady settings, vibrator(s) 146 are preferably independently powered via at least one D/C power battery 149.

Second adjuster setting 150 comprises frequency with vibrator(s) 146 comprising off, low, medium and high frequency-settings. At least one D/C power battery 149 may include 2 AA batteries or 4 AA battery units, in a longer or slightly wider module as previously mentioned. If 4 AA D/C power batteries 149 are not sufficient for user-wearer 180, larger vibration modules powered by up to 8 AA batteries will be available. It should be noted as mentioned above, in the standard V-wrap pad assembly 110 batteries 149 will preferably comprise pancake batteries. The final battery decision on the battery type will be made by manufacturer in compliance with technology changes and market demands. Each vibrator 146 can be set individually by user-wearer 180 for best results. If one of vibrators 146 wears out, vibrator 146 can be easily replaced since vibrator 146 is not integral to V-wrap pad assembly 110 and is removable. In this way the present invention is cost-effective in use.

Plurality of closers 140 preferably comprise fasteners 142 which are useable to repeatedly close and open vibrator-receiving-pocket(s) 148 and endothermic/exothermic chemical reaction gel pack-pocket(s) 156. Fasteners 142 of plurality of closers 140 comprise hook and loop said fasteners. Upon reading this specification, it should be appreciated that, under appropriate circumstances, considering such issues as user preferences, design preference, structural requirements, marketing preferences, cost, available materials, technological advances, etc., other fastener arrangements such as, for example, buttons, snaps, clips, etc., may be sufficient.

V-band therapeutic wrapping system 100 may be sold as kit 440 comprising the following parts: V-wrap pad assembly 110 with a V-wrap pad 120 with vibrator-receiving-pockets 148 and endothermic/exothermic chemical reaction gel pack-pockets 156 (both color-coded); vibrator(s) 146 (vibrating devices); endothermic/exothermic chemical reaction gel packs (heat packs and/or cold packs) 154; and a user instruction manual to indicate for example color-coded patterns as per desired treatment and the like. V-band therapeutic wrapping system 100 may be manufactured and provided for sale in a wide variety of sizes and shapes for a wide assortment of applications. Upon reading this specification, it should be appreciated that, under appropriate circumstances, considering such issues as design preference, user preferences, marketing preferences, cost, structural requirements, available materials, technological advances, etc., other kit contents or arrangements such as, for example, including more or less components, customized parts, different color combinations, parts may be sold separately, etc., may be sufficient.

Figure 7:
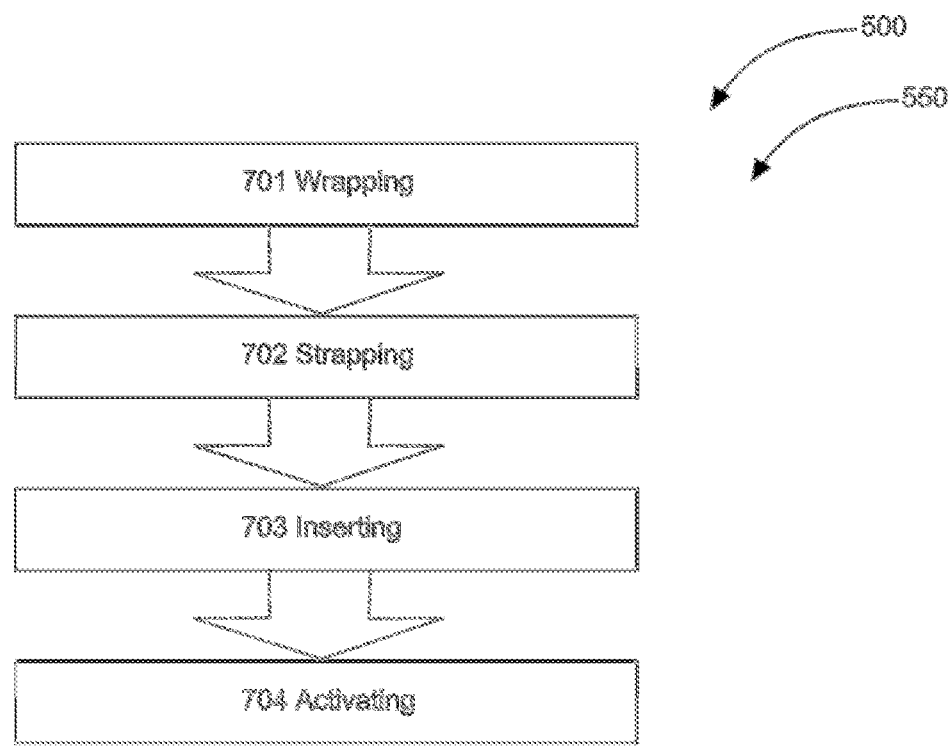
FIG. 7 is a flowchart illustrating a method of use for the V-band therapeutic wrapping system according to an embodiment of the present invention of FIGS. 1-6.

Referring now to FIG. 7, showing flowchart 550 illustrating method of use 500 for V-band therapeutic wrapping system 100 according to an embodiment of the present invention of FIGS. 1-6.

A method of using V-band therapeutic wrapping system 100 may comprise the steps of: step one 701 wrapping V-wrap pad assembly 110 about a body surface; step two 702 strapping V-wrap pad assembly 110 adjacent the body surface to therapeutically-treat a partially enveloped body region; step three 703 inserting vibrators 146 and endothermic/exothermic chemical reaction gel packs 154 into color-coded vibrator-receiving-pockets 148 and endothermic/exothermic chemical reaction gel pack-pockets 156 respectively; and step four 704 activating vibrators 146 and endothermic/exothermic chemical reaction gel pack s 154 selectively to provide relief to body region.

Referring now to FIGS. 8-13, an alternate embodiment of the "vibrator(s)" is formed as a vibration module called a "VPOD" or a "V-Pod" (800). As such the V-Pod has a curved profile, including concave front surface (810) and convex back surfaces (820) that allow it to conform to the curvature of a person's body to fit more comfortably and deliver a maximum amount of vibrations per square inch. Further the curved profile allows the user to apply a plurality of V-Pods to one body area to "surround" a chosen body part and form a "Sphere of Vibrations" around it for maximum effect and benefits. The V-Pod incorporates a rotary vibration motor (901); rechargeable batteries (902); a firmware board (903) controlling vibration velocity, intensity, and speeds; and a remote control mechanism. The V-Pods can be controlled remotely individually or in unison using a number of known methods, arrangements, and mechanisms, including computer applications software on a remote control unit or smart phone or the like. The V-Pod is charged using an associated charging base (950) having connector holsters (970) that can be plugged into a wall outlet via cord (980) or any other source that provides appropriate electric power.

Figure 8:
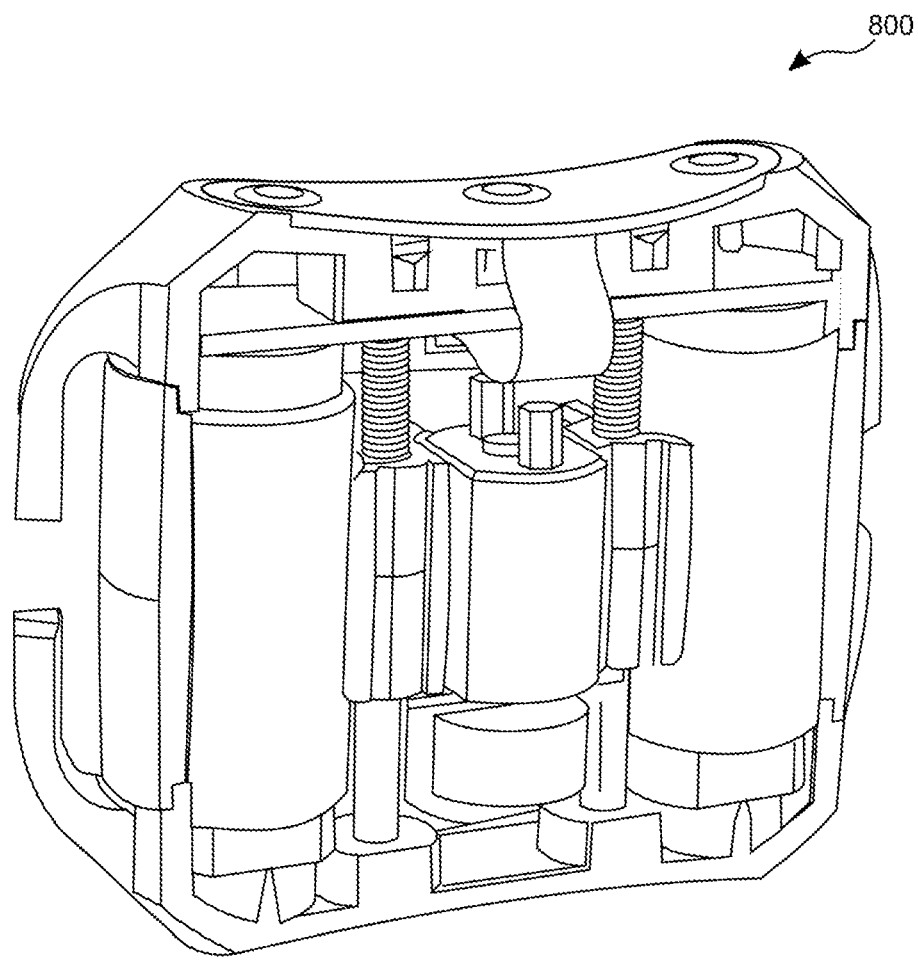
FIG. 8 shows a front perspective view an alternate embodiment of the vibrator(s) formed as a vibration module called a "VPOD" or a "V-Pod".
Figure 9:
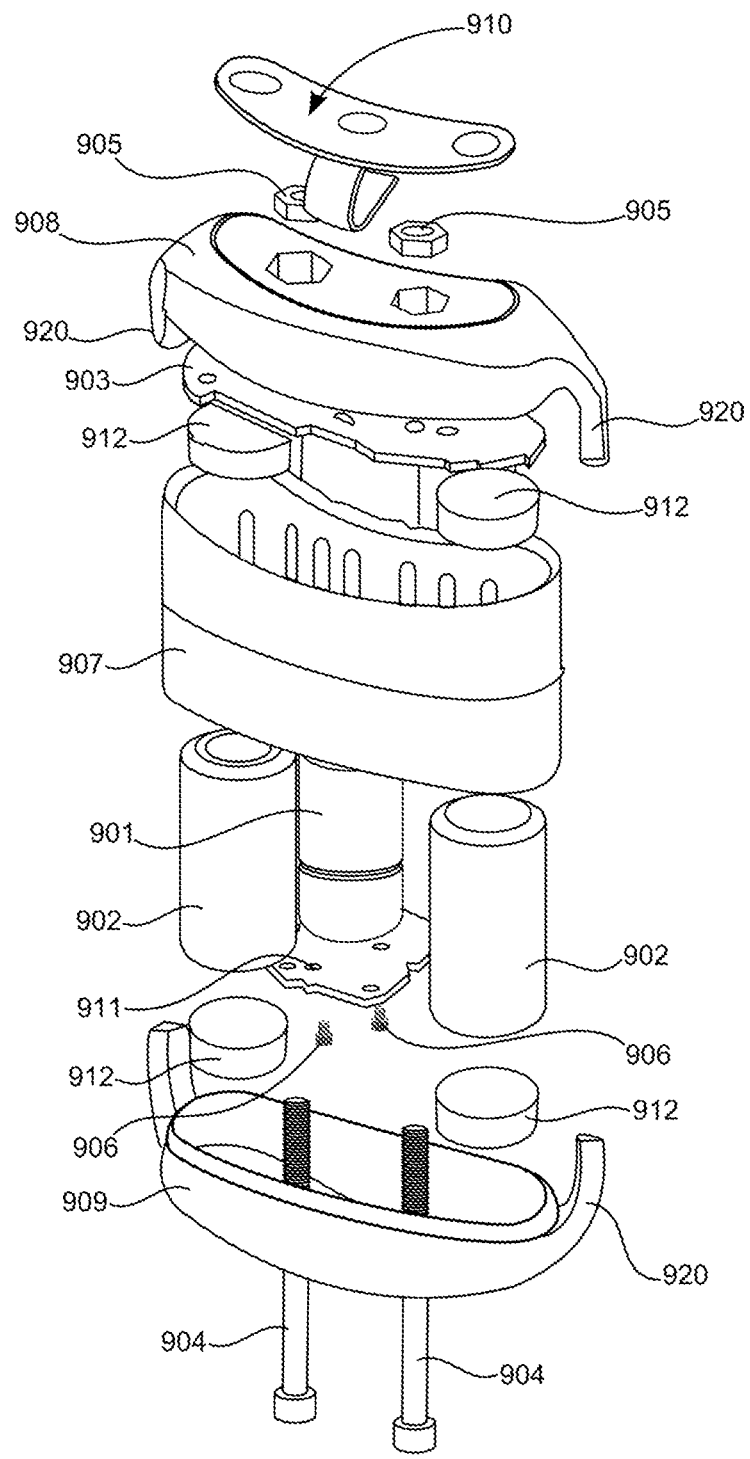
FIG. 9 shows an exploded view of the V-Pod of FIG. 8 illustrating the mechanical parts therein.
Figure 10:
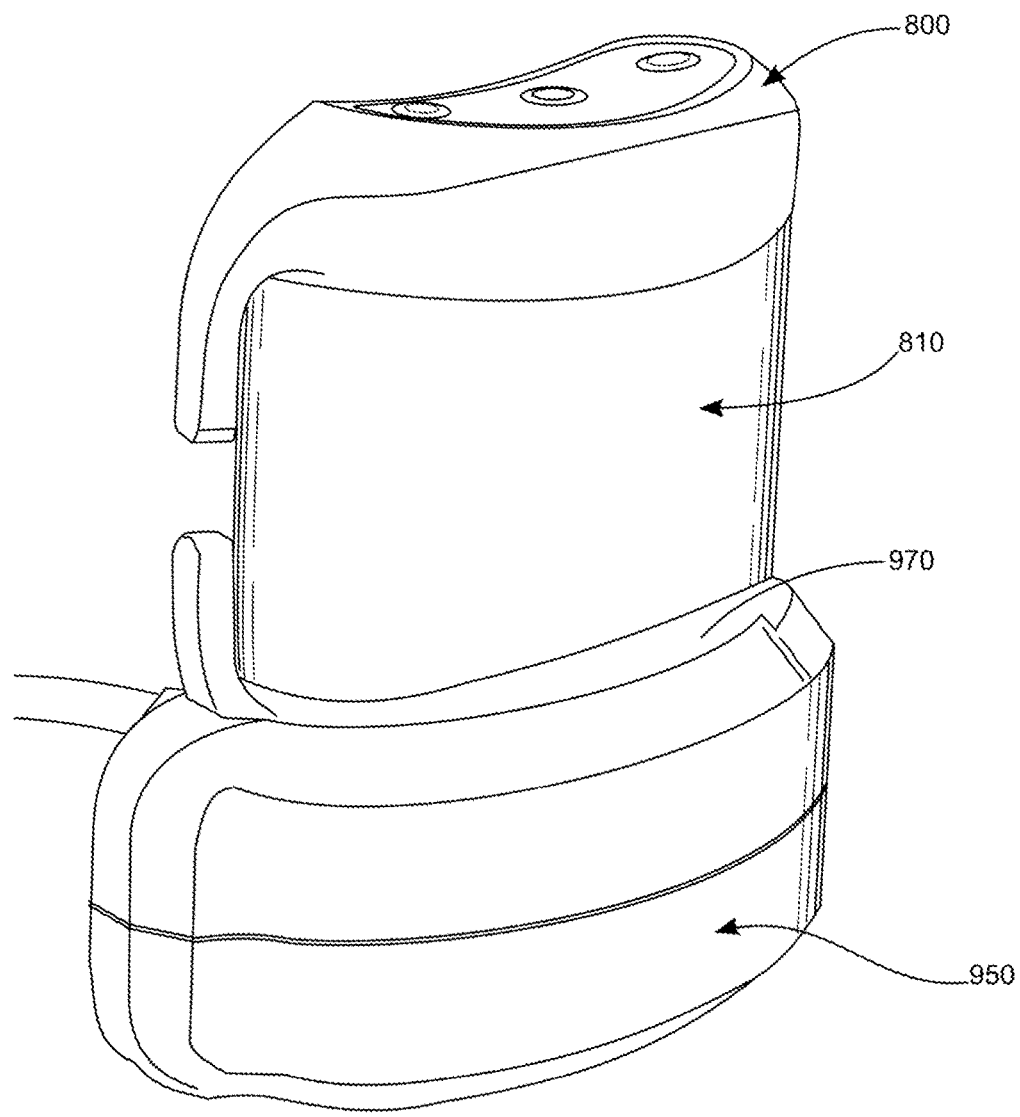
FIG. 10 shows a front perspective view of the V-Pod of FIG. 8 in an associated charging base with a plug-in nodule.
Figure 11:
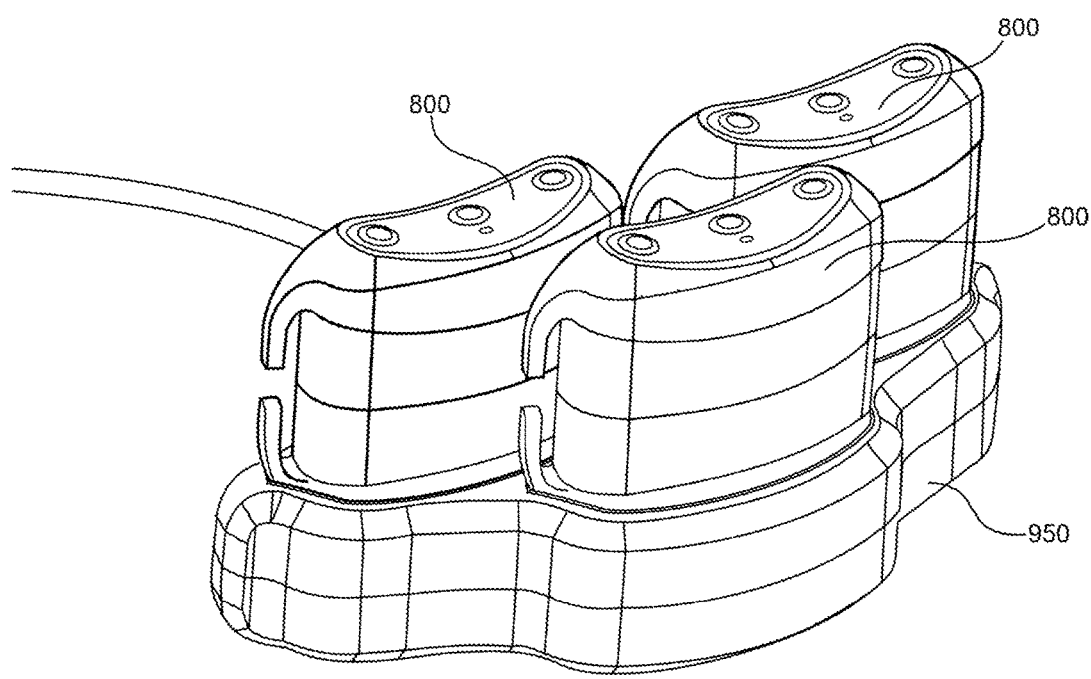
FIG. 11 shows a front perspective view of a plurality of V-Pod members of FIG. 8 in an associated charging base having a plurality of plug-in nodules.
Figure 12:
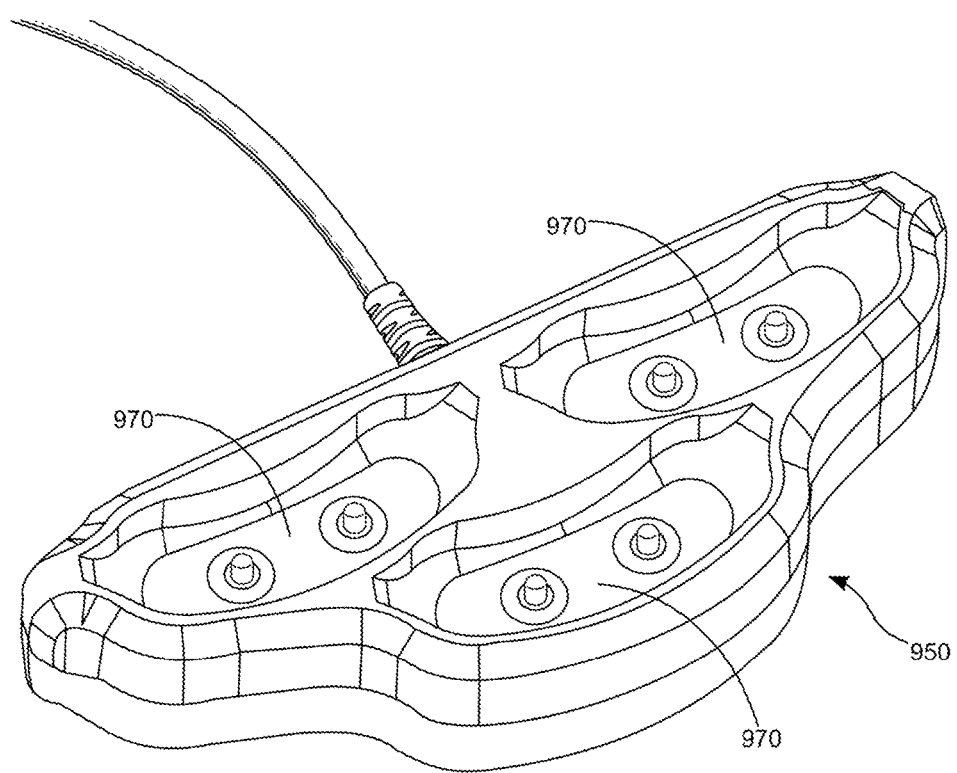
FIG. 12 shows a front perspective view of the charging base of FIG. 11 having a plurality of plug-in nodules.
Figure 13:
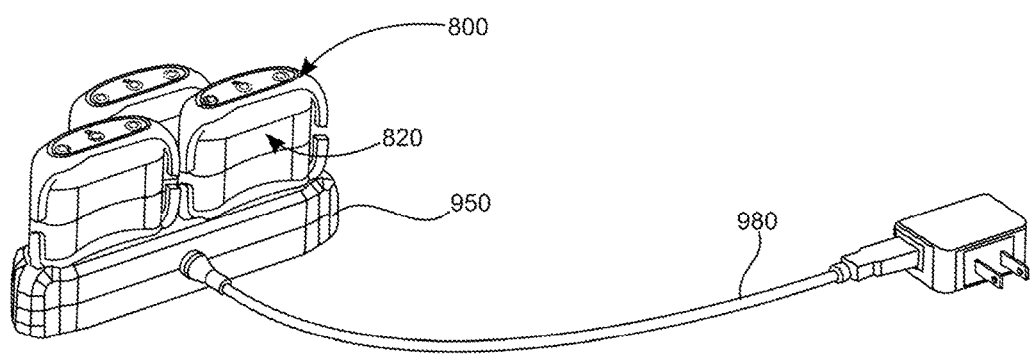
FIG. 13 shows a back perspective view of the charging base of FIG. 11 having a plurality of plug-in nodules.

As shown in FIGS. 8 and 9, the VPOD includes:

Rotary Vibration Motor (901):

Provides the vibration for the VPOD module and includes a flyweight, rotary vibration motor. This motor is capable of variable speeds. This motor type is chosen for its efficiency of output per electrical input used. Any type of present or future vibration device can be substituted in its place and still fall within the working environment of the instant invention. The vibration motor is centrally located in the VPOD for maximum impact and dispersion of vibrations throughout the device. Centrally locating the vibration motor within the VPOD makes sure that all of the surface area of the VPOD is delivering the vibrations to the user.

Rechargeable Batteries (902):

There are two of these batteries straddling the vibration motor. These batteries are used because they have the ability to provide maximum power to the vibration motor over the longest period of time with minimal power fade until the charge is exhausted. This battery also has built in circuitry to prevent over charging. This allows the use to keep the VPOD in the charging base (950) for long periods of time without damaging the batteries. The placement of the batteries on either side of the vibration motor allows for maximum balance of the VPOD. Also having the batteries in close proximity to the motor shortens the need for wires harnesses.

Any independent, portable, power source can be used in place of these rechargeable batteries, including regular batteries and solar charged batteries. Rechargeable batteries are best because they are the most efficient power source presently available.

Firmware Board (903):

This board contains the firmware to control the VPOD module. Its software has the information on how to control the motor, set the vibration velocity and motifs. There is room on the board for a second board in Phase II which will have a Bluetooth Chipset so the VPOD can be remote controlled by external control modules. Connecting the VPOD to a remote control module ca be done by Bluetooth or any present or future remote control wavelength or delivery system.

Cap Screws (904):

These cap screws are different than standard cap screws in that they are also the conductor points for recharging the batteries within the charging base (950). Any known method to recharge batteries can also be used within the VPOD configuration.

Locknuts (905):

These locknuts lock the conductor screws in place.

Flat Head Screws (906):

These screws lock the vibration motor to the securing motor plate that the conductor screws thread through to lock the motor in place. Any known method of locking the motor solidly in the vibration module/VPOD is also incorporated herein.

Main Body (907):

The main body is unique. It is ergonomically designed to fit to the human body. It is convex on one side for pinpoint pain application. It is concave on the other side to provide maximum delivery of vibration across the largest section possible. The concave application will fit comfortably against any human body area including but not inclusive of shoulders, arms, wrists, ankles, knees, back, hips, elbows, hands, thighs, and biceps. The extending arms (920) on either side of the unit allow for the threading of straps or bandages through them so that a single unit can be utilized in one specific area. The type of plastic, vinyl, or other material used is not important so long as it maximizes the transmission of vibration from the motor across its surfaces to the end user.

End Cap—Upper (908):

The upper end cap is designed to fit seamlessly to the main body and be secured by the two conductor screw securing nuts. The lipping on this cap helps provide a modicum of water resistance, protecting the interior parts. The upper end cap has a recessed section to hold and secure the button control membrane. The type of plastic, vinyl, or other material used is not important so long as it maximizes the transmission of vibration from the motor across its surfaces to the end user.

End Cap—Lower (909):

The lower end cap is designed to fit seamlessly to the main body and be secured by the two conductor screws. The lipping on this cap helps provide a modicum of water resistance, protecting the interior parts. The type of plastic, vinyl, or other material used is not important so long as it maximizes the transmission of vibration from the motor across its surfaces to the end user.

Control Panel (910):

This control panel is made to order by membrane manufacturers to control the VPOD vibration unit. It has simple buttons to control vibration velocity, and motif as well as on and off.

Motor Plate (911):

This item is for securing the vibration motor to the VPOD itself and allows for the threading of the conductor screws for securing. Any other method can be used such as spot welding, etc. This would depend on the nature of the vibration motor used.

Battery Pad (912):

This is a standard rubber pad utilized to prevent the vibrations caused by the motor from affecting the functioning or life of the power source, in this case our rechargeable batteries. These pads are utilized above and below the batteries.

"Sphere of Vibration" is a concept that we discovered during 20-years of testing. Placing a single point of contact for vibration on a joint may provide some relief, but in many cases it is insufficient. By placing points of vibration and thermos therapy in 3 or more strategic places particularly around joints, it give the feeling of encasing the affected area in a "Sphere of Vibration" and provides advanced relief.

Each person is different and will find that placing the VPODs in different places around an affected area is best for them. That is why the "Wraps" in the instant invention have numerous pockets that allow the user to put the VPODs virtually anywhere they get the most relief. With our body conforming design of the VPOD most people don't even feel the VPOD, just the vibrations. Gel packs are added to provide extra relief and feeling of comfort.

It should be noted that the steps described in the method of use can be carried out in many different orders according to user preference. The use of "step of" should not be interpreted as "step for", in the claims herein and is not intended to invoke the provisions of 35 U.S.C. § 112, ¶6. Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is:

1. An apparatus comprising
    a vibration module including:
        a housing;
        a vibration motor located centrally within the housing;
        a first battery located within the housing configured to at least partially power the vibration motor; and
        a first rubber pad located within the housing adjacent to the first battery, the first rubber pad configured to prevent vibrations from the vibration motor from affecting life of the first battery;
    wherein the housing includes a main body, an upper end cap, and a lower end cap;
    wherein the upper end cap fits seamlessly to an upper end of the main body;
    wherein the lower end cap fits seamlessly to a lower end of the main body;
    wherein the main body has a smooth closed curve outer periphery, comprised of a concave portion connected to a convex portion;

wherein the convex portion is opposite the concave portion;

wherein the upper end cap includes first and second extending arms;

wherein the lower end cap includes third and fourth extending arms;

wherein the first and third extending arms are located on a side of the housing and the second and fourth extending arms are located on an opposite side of the housing; and wherein the first, second, third, and fourth extending arms are configured to allow for threading of straps or bandages through the first, second, third, and fourth extending arms to be adapted to attach the housing to a specific area of a human body.

2. The apparatus of claim 1 wherein
the housing includes a recessed section;
and wherein the vibration module further includes a control panel which is configured to be inserted in the recessed section of the housing and held by the housing; and
wherein the control panel includes one or more buttons for controlling vibration of the vibration motor.

3. The apparatus of claim 2 further comprising
first and second cap screws;
wherein the first and second cap screws are configured so that the first and second cap screws are inserted into the housing opposite the recessed section.

4. The apparatus of claim 1 wherein
the vibration module further includes:
a second rubber pad located within the housing adjacent to the first battery, the second rubber pad configured to inhibit the vibrations from the vibration motor from affecting the functioning of the first battery; and
wherein the second rubber pad is adjacent one end of the first battery and the first rubber pad is adjacent an opposite end of the first battery.

5. The apparatus of claim 1 further comprising
a second battery located within the housing configured to at least partially power the vibration motor; and
a second rubber pad located within the housing adjacent to the second battery, the second rubber pad configured to inhibit the vibrations from the vibration motor from affecting the life of the second battery.

6. The apparatus of claim 5 wherein
the vibration module further includes:
a third rubber pad located within the housing adjacent to the first battery, the third rubber pad configured to inhibit the vibrations from the vibration motor from affecting the life of the first battery;
wherein the third rubber pad is adjacent one end of the first battery and the first rubber pad is adjacent an opposite end of the first battery; and further comprising
a fourth rubber pad located within the housing adjacent to the second battery, the fourth rubber pad configured to inhibit the vibrations from the vibration motor from affecting the life of the second battery; and
wherein the fourth rubber pad is adjacent one end of the second battery and the second rubber pad is adjacent an opposite end of the second battery.

7. An apparatus comprising
a vibration module including:
a housing;
a vibration motor located centrally within the housing;
a first battery located within the housing configured to at least partially power the vibration motor; and
a first rubber pad located within the housing adjacent to the first battery, the first rubber pad configured to prevent vibrations from the vibration motor from affecting life of the first battery;
wherein the housing includes a main body, an upper end cap, and a lower end cap;
wherein the upper end cap fits seamlessly to an upper end of the main body;
wherein the lower end cap fits seamlessly to a lower end of the main body;
wherein the main body has a smooth closed curve outer periphery, comprised of a concave portion connected to a convex portion;
wherein the convex portion is opposite the concave portion;
further comprising
a second battery located within the housing configured to at least partially power the vibration motor; and
wherein the first battery and the second battery are surrounded by the smooth closed curve outer periphery of the main body.

8. The apparatus of claim 7 wherein the first battery has a length and a width, with the length of the first battery greater than the width of the first battery;
the second battery has a length and a width, with the length of the second battery greater than the width of the second battery; and
the vibration motor has a length and a width, with the length of the vibration motor greater than the width of the vibration motor;
wherein the lengths of the first battery, the second battery, and the vibration motor are substantially parallel, and the vibration motor is located in between the first battery and the second battery.

* * * * *